(12) United States Patent
Carbone et al.

(10) Patent No.: US 12,004,823 B2
(45) Date of Patent: Jun. 11, 2024

(54) OPHTHALMIC SURGICAL SYSTEMS WITH GRAPHICAL USER INTERFACES BASED UPON SETUP CONDITIONS

(71) Applicant: Alcon Inc., Fribourg (CH)

(72) Inventors: Kyle Carbone, Chicago, IL (US); Cory Costantino, Goshen, NY (US); Sean Christopher Madden, Mission Viejo, CA (US); Prateet Verma, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 72 days.

(21) Appl. No.: 17/170,009

(22) Filed: Feb. 8, 2021

(65) Prior Publication Data

US 2021/0244488 A1 Aug. 12, 2021

Related U.S. Application Data

(60) Provisional application No. 62/975,228, filed on Feb. 12, 2020.

(51) Int. Cl.
*A61B 34/00* (2016.01)
*A61B 90/00* (2016.01)
*A61F 9/007* (2006.01)
*A61F 9/008* (2006.01)

(52) U.S. Cl.
CPC ............. *A61B 34/25* (2016.02); *A61F 9/007* (2013.01); *A61B 2034/254* (2016.02); *A61B 2090/372* (2016.02); *A61B 2217/005* (2013.01); *A61F 9/008* (2013.01)

(58) Field of Classification Search
CPC .............. A61B 34/25; A61B 2034/254; A61B 2090/372; A61B 2217/005; A61F 9/007; A61F 9/008; A61F 9/00736
See application file for complete search history.

(56) References Cited

U.S. PATENT DOCUMENTS

| | | | |
|---|---|---|---|
| 6,251,113 B1 * | 6/2001 | Appelbaum | A61B 50/13 606/1 |
| 9,931,447 B2 | 4/2018 | Layser | |
| 2002/0001307 A1 * | 1/2002 | Nguyen | H04L 41/0856 370/386 |

(Continued)

FOREIGN PATENT DOCUMENTS

EP 2298221 A1 3/2011

*Primary Examiner* — Michael Roswell
(74) *Attorney, Agent, or Firm* — PATTERSON + SHERIDAN, LLP (57) ABSTRACT

Ophthalmic surgical systems and methods for displaying graphical user interfaces in ophthalmic surgical systems are disclosed. An example ophthalmic surgical system has alternative setup conditions, and a host computer is configured to detect the setup condition and to display on a display screen a graphical user interface corresponding to the detected setup condition. The alternative setup conditions may be based upon a configuration of an ophthalmic surgical console and/or based upon which type of fluidics cassette is installed on the ophthalmic surgical console. In some embodiments, the host computer is configured to display on the display screen a graphical user interface that graphically indicates the instrument ports that are available and/or that are not available for instrument connections in the detected setup condition.

16 Claims, 2 Drawing Sheets

(56) References Cited

U.S. PATENT DOCUMENTS

| | | | |
|---|---|---|---|
| 2004/0169673 A1* | 9/2004 | Crampe | A61B 34/20 |
| | | | 600/300 |
| 2007/0202479 A1* | 8/2007 | Todd | A61B 50/13 |
| | | | 434/262 |
| 2019/0206563 A1* | 7/2019 | Shelton, IV | B25J 13/006 |
| 2020/0081585 A1* | 3/2020 | Petre | G06F 3/14 |
| 2021/0145526 A1* | 5/2021 | Robinson | A61B 34/37 |

* cited by examiner

OPHTHALMIC SURGICAL SYSTEMS WITH GRAPHICAL USER INTERFACES BASED UPON SETUP CONDITIONS

TECHNICAL FIELD

This disclosure is directed to ophthalmic surgical systems and graphical user interfaces for ophthalmic surgical systems.

BACKGROUND

Ophthalmic surgical systems are employed for performing various types of ophthalmic procedures. For example, ophthalmic surgical systems are available for cataract surgery, providing functionality for the operator to perform the steps necessary for cataract surgery and related procedures. As another example, ophthalmic surgical systems are available for vitreoretinal surgery, providing functionality for the operator to perform the steps necessary for vitreoretinal surgery and related procedures.

Some prior ophthalmic surgical systems have graphical user interfaces for conveying information to the user and in some case for allowing the user to interact with the system. For example, the graphical user interface may show various functions, and actuation of a control such as a footswitch may enable scrolling through or switching between functions indicated on the graphical user interface.

While prior ophthalmic surgical systems have been useful for their purposes, there is a continuing need for improved ophthalmic surgical systems and graphical user interfaces for ophthalmic surgical systems.

SUMMARY

The present disclosure is directed to improved ophthalmic surgical systems and methods for displaying graphical user interfaces in an ophthalmic surgical system.

In some embodiments, an ophthalmic surgical system comprises an ophthalmic surgical console comprising a host computer, a display screen, and a plurality of instruments configured to be connected to the ophthalmic surgical console, wherein the ophthalmic surgical system has a plurality of alternative setup conditions, and wherein the host computer is configured to detect the setup condition of the ophthalmic surgical system and to display on the display screen a graphical user interface corresponding to the detected setup condition. The display screen may be part of the ophthalmic surgical console or a separate component. In some embodiments, the alternative setup conditions of the ophthalmic surgical system include two or more of the following conditions: an anterior-only condition, a posterior-only condition, and an anterior-posterior or combined function condition. In some embodiments, the ophthalmic surgical console may be capable of being configured as an anterior-only machine or as an anterior-posterior or combined function machine, wherein the alternative setup conditions of the ophthalmic surgical system include an anterior-only condition when the ophthalmic surgical console is configured as an anterior-only machine and an anterior-posterior or combined function condition when the ophthalmic surgical console is configured as an anterior-posterior or combined function machine.

In some embodiments, the ophthalmic surgical system may further comprise a plurality of fluidics cassettes that are configured to be installed on the ophthalmic surgical console. The ophthalmic surgical console may be configured to have installed on it one fluidics cassette at a time. The alternative setup conditions of the ophthalmic surgical system may include alternative setup conditions based upon which cassette of the plurality of fluidics cassettes is installed on the ophthalmic surgical console. The plurality of fluidics cassettes may include two or more of the following: an anterior-only cassette, a posterior-only cassette, and an anterior-posterior or combined function cassette. The alternative setup conditions of the ophthalmic surgical system may include two or more of the following conditions: an anterior-only condition when an anterior-only cassette is installed on the ophthalmic surgical console, a posterior-only condition when a posterior-only cassette is installed on the ophthalmic surgical console, and an anterior-posterior or combined function condition when an anterior-posterior or combined function cassette is installed on the ophthalmic surgical console.

The ophthalmic surgical console may comprise a plurality of instrument ports to which the plurality of instruments may be connected. In some embodiments, the host computer is configured to display on the display screen a graphical user interface that graphically indicates the instrument ports that are available and/or that are not available for instrument connections in the detected setup condition of the ophthalmic surgical system. In some embodiments, the host computer is configured to display on the display screen a graphical user interface that graphically indicates the instrument ports to which instruments are connected.

In some embodiments, a method of displaying a graphical user interface in an ophthalmic surgical system comprises detecting a setup condition of the ophthalmic surgical system from a plurality of alternative setup conditions of the ophthalmic surgical system, and displaying on a display screen a graphical user interface corresponding to the detected setup condition. The alternative setup conditions of the ophthalmic surgical system may include two or more of the following conditions: an anterior-only condition, a posterior-only condition, and an anterior-posterior or combined function condition. The ophthalmic surgical system may comprise a ophthalmic surgical console, wherein the ophthalmic surgical console may be capable of being configured at least as an anterior-only machine or as an anterior-posterior or combined function machine, and wherein the alternative setup conditions of the ophthalmic surgical system may include an anterior-only condition when the ophthalmic surgical console is configured as an anterior-only machine and an anterior-posterior or combined function condition when the ophthalmic surgical console is configured as an anterior-posterior or combined function machine. In some embodiments, the method may further comprise, prior to the step of detecting a setup condition of the ophthalmic surgical system, installing a fluidics cassette on an ophthalmic surgical console of the ophthalmic surgical system, wherein the step of detecting a setup condition of the ophthalmic surgical system comprises detecting a setup condition of the ophthalmic surgical system based upon which cassette of a plurality of fluidics cassettes is installed on the ophthalmic surgical console. In some embodiments, the step of displaying on a display screen a graphical user interface corresponding to the detected setup condition may comprise graphically indicating instrument ports that are available and/or that are not available for instrument connections in the detected setup condition of the ophthalmic surgical system. In some embodiments, the step of displaying on a display screen a graphical user interface corresponding to the detected setup condition may comprise graphically indicating instrument ports to which instruments are connected.

The above examples and other examples will be understood by persons having ordinary skill in the art based on this disclosure.

BRIEF DESCRIPTION OF THE DRAWINGS

The accompanying drawings illustrate examples of systems and methods as disclosed herein and, together with the description, serve to explain the principles of the disclosure.

The accompanying drawings may be better understood by reference to the following detailed description.

DETAILED DESCRIPTION

For the purposes of explaining the principles of the disclosure, reference is made to the drawings, and specific language is used to describe the same. It will nevertheless be understood that, by reference to certain examples, no limitation of the scope of the disclosure is intended. Any alterations and further modifications to the described example systems, devices, instruments, and methods, and any further application of the principles of the disclosure, are fully contemplated as would normally occur to one skilled in the art to which the disclosure relates. In particular, the features, components, and/or steps described with respect to one example of the disclosure may be combined with features, components, and/or steps described with respect to other examples of the disclosure and may be modified and/or substituted as would normally occur to one skilled in the art. For simplicity, in some instances the same reference numbers may be used throughout the drawings to refer to the same or like parts.

Figure 1:
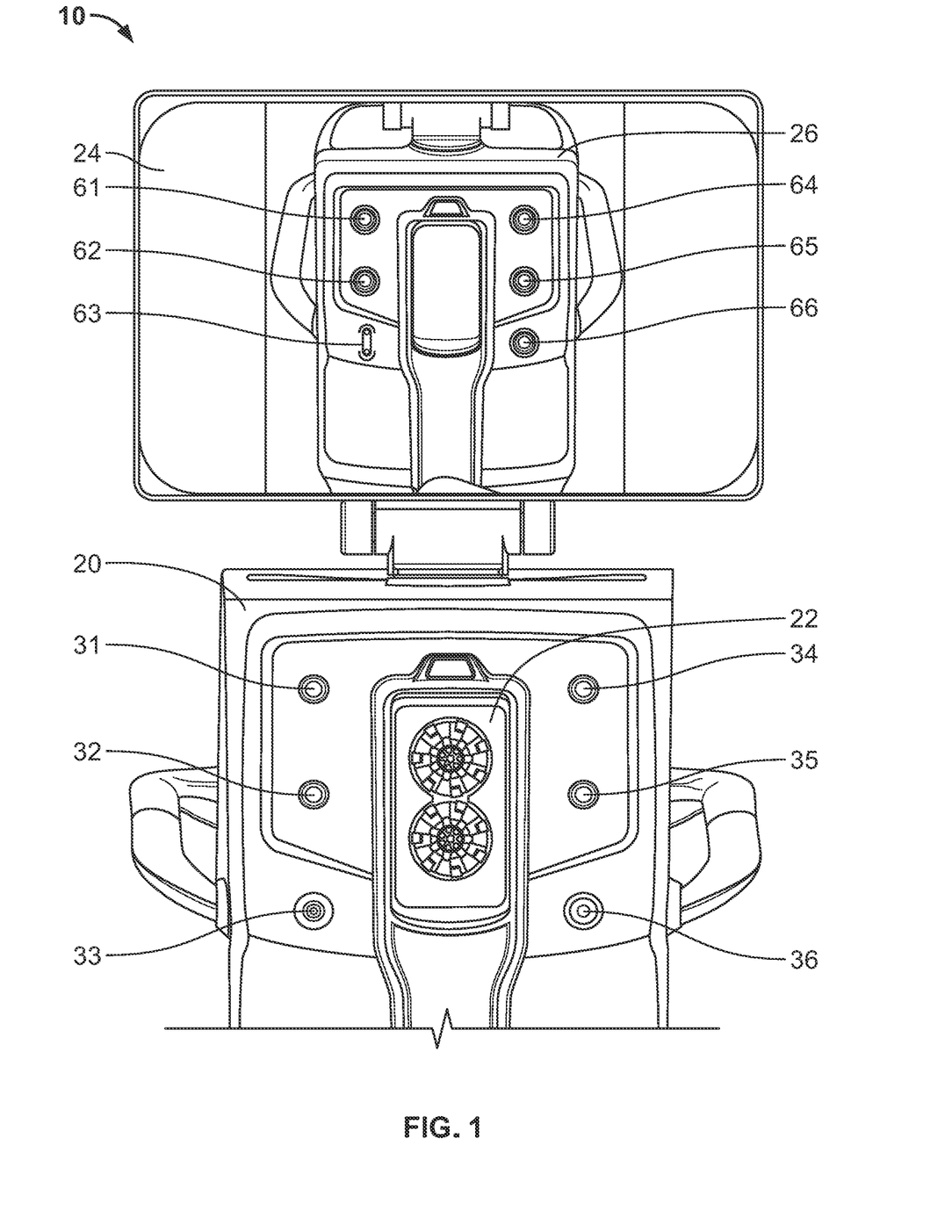
FIG. 1 illustrates an example ophthalmic surgical system in a first setup condition with a corresponding graphical user interface in accordance with the disclosure.
Figure 2:
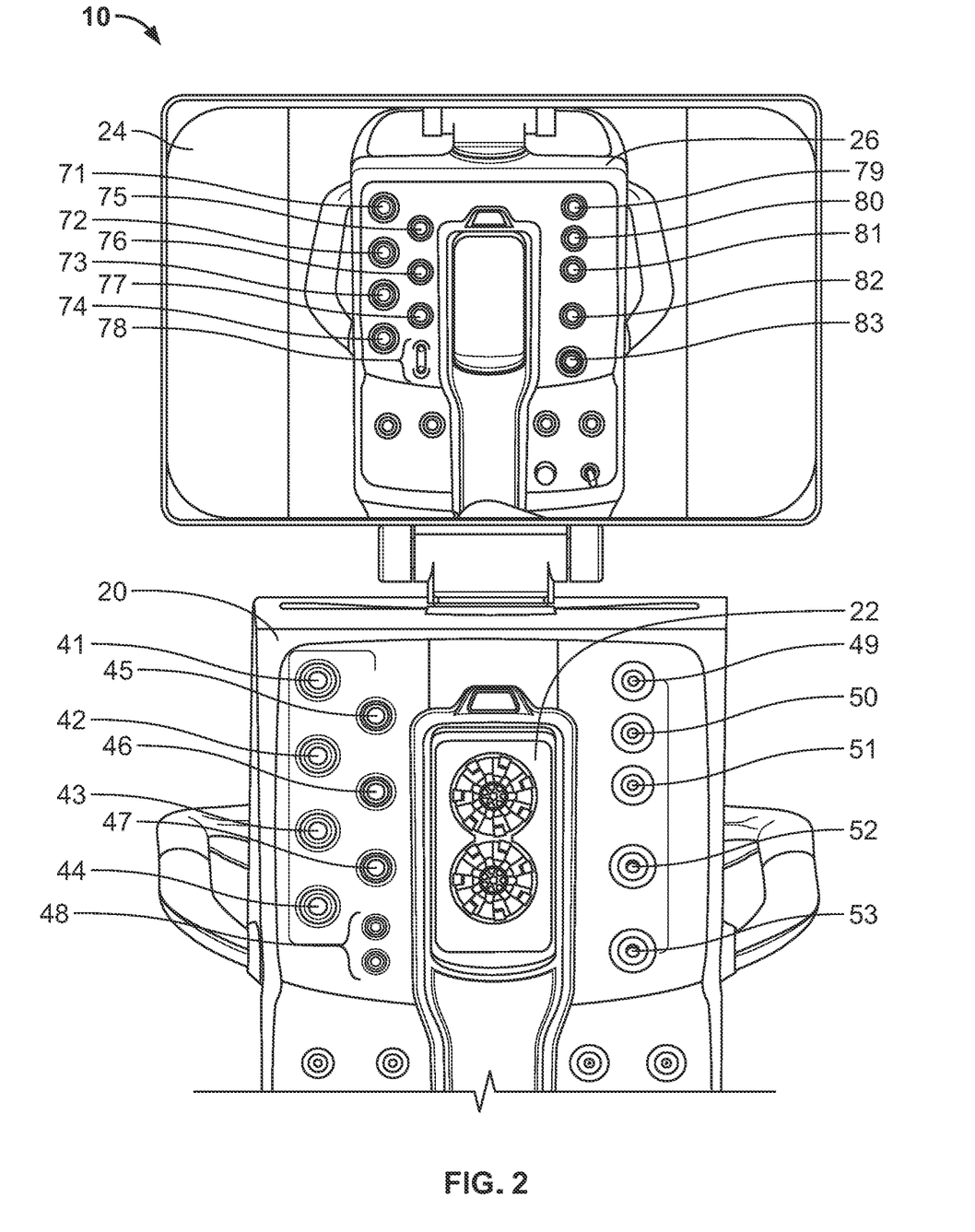
FIG. 2 illustrates the example ophthalmic surgical system in a second setup condition with a corresponding graphical user interface in accordance with the disclosure.

FIG. 1 illustrates an example ophthalmic surgical system 10 in a first setup condition, while FIG. 2 illustrates the example ophthalmic surgical system 10 in a second setup condition. The ophthalmic surgical system 10 is a system that may be used for ophthalmic surgical procedures such as cataract surgery and/or retinal surgery. These procedures may include procedures such as phacoemulsification, coagulation, vitrectomy, retinopathy, and/or other procedures.

As illustrated in FIGS. 1 and 2, the ophthalmic surgical system 10 includes an ophthalmic surgical console 20 and a display screen 24. The display screen 24 may be part of the ophthalmic surgical console 20, or it may be a separate component. The ophthalmic surgical console 20 houses a host computer as well as components for various functions for performing ophthalmic surgical procedures. The ophthalmic surgical system 10 also may include a footswitch (not shown) that has one or more switches and/or buttons that can be actuated by foot to enable the operator to control certain functions of the ophthalmic surgical system 10. Actuation of the footswitch or another control may enable scrolling through or switching between functions indicated on the display screen 24 and/or may control such functions as the flow of fluidics, aspiration rate, phacoemulsification power, vitrectomy cut rate, intraocular lens injection rate, anterior capsulotomy, laser activation, and/or coagulation power.

The ophthalmic surgical system 10 may further comprise one or more fluidics cassettes (not shown) configured to be installed on the ophthalmic surgical console 20. The ophthalmic surgical console has a fluidics cassette dock 22 to which a fluidics cassette may be installed. In the illustrated embodiment, the ophthalmic surgical console 20 houses a motor that controls the action of a plurality of rollers that can be used to press upon an elastomeric fluid channel of a fluidics cassette in order to generate a pumping action, for example for aspiration of fluid and/or other materials from the eye.

The ophthalmic surgical system 10 may further comprise a plurality of instruments configured to be connected to the ophthalmic surgical console 20. The ophthalmic surgical console 20 has a plurality of instrument ports, labeled 31-36 in the configuration of FIGS. 1 and 41-53 in the configuration of FIG. 2, to which instruments may be connected.

In the illustrated embodiment, the ophthalmic surgical system 10 has a modular design by which it can be set up in multiple configurations. For example, in a first configuration, as shown in FIG. 1, the ophthalmic surgical system 10 may be configured as an "anterior-only" machine, for performing cataract surgery and related procedures, and in a second configuration, as shown in FIG. 2, the ophthalmic surgical system 10 may be configured as an "anterior-posterior" or "combined function" machine, for performing cataract surgery and related procedures as well as vitreoretinal surgery and related procedures. While the terms "anterior" and "posterior" are meant to refer generally to the anterior and posterior chambers of the eye, persons of ordinary skill in the art will understand that the locations of the procedures performed are not necessarily limited to the anterior chamber or the posterior chamber, but instead should include some or all of the procedures typically associated with cataract surgery and related procedures for "anterior-only" machines and some or all of the procedures typically associated with cataract surgery and related procedures as well as some or all of the procedures typically associated with vitreoretinal surgery and related procedures for "anterior-posterior" or "combined function" machines. The terms "anterior-posterior" and "combined function" are used interchangeably herein and are meant to refer to a configuration suitable for performing some or all of the procedures typically associated with cataract surgery and related procedures as well as some or all of the procedures typically associated with vitreoretinal surgery and related procedures. In some situations, a combined function system, machine, console, or cassette may also be referred to as a "dual function" system, machine, console, or cassette.

The procedures that may be performed using the ophthalmic surgical system 10 when it is configured as an anterior-only machine may include procedures such as phacoemulsification, coagulation, and vitrectomy (e.g., anterior vitrectomy), for example. The procedures that may be performed using the ophthalmic surgical system 10 when it is configured as an anterior-only machine may include procedures that are typically performed using existing cataract surgery systems, such as the CENTURION® Vision System available from Alcon Laboratories, Inc. (Fort Worth, Texas). The procedures may include procedures that may be performed using ophthalmic surgical systems similar to ophthalmic surgical systems as shown and described in U.S. Pat. No. 9,931,447, which is hereby incorporated by reference herein in its entirety.

The procedures that may be performed using the ophthalmic surgical system 10 when it is configured as a combined function machine may include all of the procedures of an anterior-only machine as well as vitrectomy (e.g., posterior vitrectomy), retinopathy, and other vitreoretinal procedures, for example. The procedures that may be performed using the ophthalmic surgical system 10 when it is configured as a combined function machine may include procedures that are typically performed using existing cataract surgery systems, such as the CENTURION® Vision System, as well as procedures that are typically performed using existing vitreoretinal surgery systems, such as the CONSTELLATION® Vision System, also available from Alcon Laboratories, Inc. (Fort Worth, Texas).

The modular design of the ophthalmic surgical system 10 may be accomplished by the ophthalmic surgical console 20 being capable of accommodating different functional modules in accordance with the desired configuration. For example, in an anterior-only configuration, the ophthalmic surgical console 20 may include modules for ultrasound (e.g., for phacoemulsification), diathermy, and/or pneumatics, while in a combined function configuration, the ophthalmic surgical console 20 may include these modules as well as modules for laser therapy, illumination, nano-illumination, and/or other pneumatic functions.

While the ophthalmic surgical system 10 has been described as having anterior-only and combined function configurations, an ophthalmic surgical system in accordance with the disclosure may have other configurations for incorporating different functions or combinations of functions. For example, the ophthalmic surgical system 10 may have a "posterior-only" configuration for performing some or all of the procedures typically associated with vitreoretinal surgery and related procedures but not cataract surgery. As another example, the ophthalmic surgical system 10 may have alternative types of setup conditions within the categories of anterior-only, posterior-only, or combined function. For example, the ophthalmic surgical console 20 may be configurable in a combined function configuration without a tray and laser, without a tray (but with a laser), without a laser (but with a tray), or "fully loaded" with all available functionality.

As mentioned above, the ophthalmic surgical system 10 may comprise one or more fluidics cassettes (not shown) that are configured to be installed at the fluidics cassette dock 22 of the ophthalmic surgical console 20. The plurality of fluidics cassettes may include an anterior-only cassette for anterior-only procedures as described above, a posterior-only cassette for posterior-only procedures as described above, and an anterior-posterior or combined function cassette for anterior-posterior or combined function procedures as described above. The ophthalmic surgical system 10 may include any one of these fluidics cassettes or any combination of them. For example, the plurality of fluidics cassettes may include two or more of the following: an anterior-only cassette, a posterior-only cassette, and an anterior-posterior or combined function cassette. In the illustrated embodiment, only one fluidics cassette of the plurality of fluidics cassette may be installed on the ophthalmic surgical console 20 at a time.

In accordance with the disclosure, an ophthalmic surgical system as described herein has a plurality of alternative setup conditions. The alternative setup conditions may be due to different machine configurations and/or due to different installed fluidics cassettes. For example, the ophthalmic surgical console may be capable of being configured as an anterior-only machine, a posterior-only machine, or a combined function machine. In such an example, the alternative setup conditions of the ophthalmic surgical system include an anterior-only condition when the ophthalmic surgical console is configured as an anterior-only machine, a posterior-only condition when the ophthalmic surgical console is configured as an posterior-only machine, and a combined function condition when the ophthalmic surgical console is configured as a combined function machine. In another example, the ophthalmic surgical console may be capable of being configured as any two of an anterior-only machine, a posterior-only machine, and a combined function machine. For example, the ophthalmic surgical console may be capable of being configured as an anterior-only machine or a combined function machine. In such an example, the alternative setup conditions of the ophthalmic surgical system include an anterior-only condition when the ophthalmic surgical console is configured as an anterior-only machine and a combined function condition when the ophthalmic surgical console is configured as a combined function machine. As mentioned above, the ophthalmic surgical system 10 may have alternative types of setup conditions within the categories of anterior-only, posterior-only, or combined function (such as with or without a tray and/or laser).

The alternative setup conditions additionally or alternatively may be based upon which cassette of the plurality of fluidics cassettes is installed on the ophthalmic surgical console. For example, the alternative setup conditions of the ophthalmic surgical system may include two or more of the following conditions: an anterior-only condition when an anterior-only cassette is installed on the ophthalmic surgical console, a posterior-only condition when a posterior-only cassette is installed on the ophthalmic surgical console, and a combined function condition when a combined function cassette is installed on the ophthalmic surgical console. In one example embodiment, the ophthalmic surgical console may have multiple machine configurations and may accommodate different fluidics cassettes, and the alternative setup conditions of the ophthalmic surgical system may be based upon the machine configuration of the ophthalmic surgical console and upon which cassette of the plurality of fluidics cassettes is installed on the ophthalmic surgical console. In another example embodiment, the ophthalmic surgical console may have only a single configuration, for example a combined function configuration, and the alternative setup conditions of the ophthalmic surgical system may be based solely upon which cassette of the plurality of fluidics cassettes is installed on the ophthalmic surgical console. For example, an ophthalmic surgical system with an ophthalmic surgical console having only a combined function configuration may have an anterior-only condition when an anterior-only cassette is installed on the ophthalmic surgical console, a posterior-only condition when a posterior-only cassette is installed on the ophthalmic surgical console, and a combined function condition when a combined function cassette is installed on the ophthalmic surgical console. The types of ophthalmic surgical consoles and fluidics cassettes described herein may be combined in any combination yielding different sets of alternative setup conditions for the ophthalmic surgical system.

In an example, the alternative setup conditions for the ophthalmic surgical system are based upon the configuration of the ophthalmic surgical console and the type of fluidics cassette that is installed, if any. For example, the ophthalmic surgical console may have anterior-only and combined function configurations, wherein the ophthalmic surgical console has the following different types of combined function configurations: without tray and laser, without tray but with laser, without laser but with tray, and fully loaded with tray and laser. Continuing with this example, when the ophthalmic surgical console is in an anterior-only configuration, an anterior-only cassette may be installed or there may be no cassette installed. Similarly, when the ophthalmic surgical console is in one of the combined function configurations, an anterior-only cassette may be installed, a posterior-only cassette may be installed, a combined function cassette may be installed, or there may be no cassette installed. In each case, the host computer detects the setup condition of the ophthalmic surgical system based upon the configuration of the ophthalmic surgical console and the type of fluidics cassette that is installed, if any.

As described above, the ophthalmic surgical console 20 comprises a plurality of instrument ports to which the plurality of instruments may be connected. Different setup conditions of the ophthalmic surgical system 10 may have different instruments associated with them. For example, in an anterior-only configuration, the ophthalmic surgical console 20 may include instrument ports for one or more ultrasound instruments (e.g., one or more phacoemulsification handpieces), one or more electrical diathermy instruments, and/or one or more pneumatic instruments (e.g., one or more vitrectomy instruments). In a posterior-only configuration, the ophthalmic surgical console 20 may include instrument ports for one or more pneumatic instruments (e.g., one or more vitrectomy instruments), one or more laser instruments, and/or one or more illumination instruments (e.g., one or more illuminators and/or nano-illuminators). In a combined function configuration, the ophthalmic surgical console 20 may include the instrument ports of both the anterior-only configuration and the posterior-only configuration.

In FIG. 1, the ophthalmic surgical console 20 is in the first machine configuration and has a plurality of instrument ports 31-36. As an example, instrument ports 31 and 32 may be instrument ports for ultrasound instruments, instrument port 33 may be an instrument port for a diathermy instrument, instrument ports 34 and 35 may be ports for air infusion instruments, and instrument port 36 may be an instrument port for a pneumatic instrument. Numerous other variations of instrument ports and combinations of instrument ports are possible.

In FIG. 2, the ophthalmic surgical console 20 is in the second machine configuration and has a plurality of instrument ports 41-53. As an example, instrument ports 41, 42, 43, and 44 may be instrument ports for ultrasound instruments, instrument port 45 may be an instrument port for a laser instrument, instrument ports 46 and 47 may be instrument ports for illumination instruments, instrument port 48 may be an instrument port for a diathermy instrument, instrument ports 49, 50, and 51 may be instrument ports for pneumatically-driven tools such as one or more visco-fluid cutters, forceps, and/or scissors, instrument port 52 may be a port for an air infusion instruments, and instrument port 53 may be an instrument port for a vitrectomy instrument. Numerous other variations of instrument ports and combinations of instrument ports are possible.

The host computer includes one or more processors as well as software and is configured to detect automatically the setup condition of the ophthalmic surgical system 10 and to display on the display screen 24 a graphical user interface 26 corresponding to the detected setup condition. For example, the software may be intelligent to recognize the configuration of the ophthalmic surgical console 20, for example based upon the modules included in the ophthalmic surgical console 20. If an ophthalmic surgical console 20 is modified by removing, replacing, or adding one or more modules, the host computer software can recognize the new configuration and display an associated graphical user interface. Additionally or alternatively, the software may be intelligent to recognize the type of fluidics cassette that is installed, if any. The fluidics cassette may have a bar code, RFID chip, or other machine-readable indicia or feature by which the host computer can detect which type of fluidics cassette is installed, if any, and, accordingly, the host computer can display an associated graphical user interface.

The host computer is configured to display on the display screen 24 a graphical user interface 26 that graphically indicates the instrument ports that are available for instrument connections in the detected setup condition of the ophthalmic surgical system 10. For example, based upon the detected setup condition, the available instrument ports may include all or less than all of the physical instrument ports on the ophthalmic surgical console 20.

For example, in FIG. 1 with the ophthalmic surgical console 20 in an anterior-only configuration, the ophthalmic surgical console 20 may accept only an anterior-only fluidics cassette, if any. The host computer detects the setup condition as an anterior-only setup condition and displays on the display screen 24 a graphical user interface 26 that graphically indicates the instrument ports that are available for instrument connections in the detected anterior-only setup condition. Thus, the graphical user interface 26 in FIG. 1 has icons 61-66 corresponding to instrument ports 31-36, and it graphically shows all of these ports as available.

In FIG. 2 with the ophthalmic surgical console 20 in a combined function configuration, the ophthalmic surgical console 20 may accept either an anterior-only fluidics cassette, a posterior-only fluidics cassette, or a combined function fluidics cassette, if any. The host computer detects the setup condition based upon the machine configuration and installed fluidics cassette and displays on the display screen 24 a graphical user interface 26 that graphically indicates the instrument ports that are available for instrument connections in the detected setup condition. The graphical user interface 26 in FIG. 2 has icons 71-83 corresponding to instrument ports 41-53, and the graphical user interface will show which ports are available based upon the detected setup condition.

If, for example, a fluidics cassette is installed for which less than all of the instrument ports may be used, the graphical user interface 26 may indicate ports that are unavailable and/or available. For example, if the ophthalmic surgical console 20 is in a combined function configuration and an anterior-only fluidics cassette is installed, the icons associated with instrument ports that are not available in an anterior-only setup may be shown as unavailable, for example greyed out or ghosted or in dashed lines. Similarly, the icons associated with instrument ports that are available in an anterior-only setup may be shown as available, for example highlighted or in solid lines or not greyed out or ghosted. Thus, for example, if the ophthalmic surgical console 20 is in a combined function configuration and an anterior-only fluidics cassette is installed, the icons 75-77 (corresponding to laser and illumination instrument ports 45-47) and the icons 79-81 (corresponding to instrument ports for one or more visco-fluid cutters, forceps, and/or scissors) may be shown as unavailable, while the remaining icons 71-74 (corresponding to ultrasound instrument ports 41-44), 78 (corresponding to diathermy instrument port 48), and 82-83 (corresponding to air infusion instrument port 52 and vitrectomy instrument ports 53) are shown as available. In another example, if the ophthalmic surgical console 20 is in a combined function configuration and a combined function fluidics cassette is installed, all icons 71-83 may be shown as available.

Once a user connects an instrument to an instrument port, the host computer can detect the connection and can indicate on the graphical user interface 26 that an instrument has been connected to that instrument port. The connector of the instrument may have an RFID tag or other machine-readable feature, and each instrument port may have an RFID reader or other component for reading the machine-readable feature of the instrument connector. In this way, the host computer can determine that an instrument has been connected and can determine which type of instrument has been connected, including whether an instrument proper for the particular port has been connected to the port. The host computer can detect the connection and can indicate on the graphical user interface 26 that an improper instrument has been connected to the instrument port or that a proper instrument has been connected to the instrument port. For example, the icon corresponding to the instrument port to which an instrument has been connected may be changed to indicate an improper or proper connection, for example by changing color, adding a ring, blinking, etc.

In some cases, another step may be required before a properly connected instrument is ready to be used. For example, a connected instrument may need to be primed before it is ready to be used. The host computer can detect when a connected instrument is ready to be used and can indicate on the display screen 24 that the instrument is ready. For example, the icon corresponding to the instrument port to which an instrument has been connected and is ready to be used may be changed to indicate the readiness of the instrument, for example by changing color, adding a ring, blinking, etc.

In one example, no color or greying-out of an icon may be used to indicate that an instrument port is unavailable, a blue ring around the graphical representation of an instrument port may be used to indicate that a port is available, a blinking green ring around the graphical representation of an instrument port may be used to indicate that an instrument has been connected but another step (e.g., priming) is needed before the connected instrument is ready to be used, and a steady (non-blinking) green ring around the graphical representation of an instrument port may be used to indicate that the connected instrument is ready to be used. Many other variations are possible.

An example method of displaying a graphical user interface in an ophthalmic surgical system is as follows. First, the host computer detects a setup condition of the ophthalmic surgical system from a plurality of alternative setup conditions of the ophthalmic surgical system. The alternative setup conditions may be based upon the configuration of the ophthalmic surgical console and/or upon the type of fluidics cassette installed on the ophthalmic surgical console, if any. Second, the host computer causes to be displayed on a display screen a graphical user interface corresponding to the detected setup condition.

Prior to the step of detecting a setup condition of the ophthalmic surgical system, a user may install a fluidics cassette on an ophthalmic surgical console of the ophthalmic surgical system. The step of detecting a setup condition of the ophthalmic surgical system may comprise detecting a setup condition of the ophthalmic surgical system based upon which cassette of a plurality of fluidics cassettes is installed on the ophthalmic surgical console.

The step of displaying on a display screen a graphical user interface corresponding to the detected setup condition may comprise graphically indicating instrument ports that are available for instrument connections in the detected setup condition of the ophthalmic surgical system. The step of displaying on a display screen a graphical user interface corresponding to the detected setup condition may comprise graphically indicating instrument ports that are available and/or not available for instrument connections in the detected setup condition, instrument ports to which instruments have been connected, and/or instrument ports to which ready-for-use instruments are connected.

Persons having ordinary skill in the art will recognize that systems and methods as disclosed herein have one or more advantages over prior approaches. For example, in comparison with prior approaches, systems and methods as disclosed involve the use of ophthalmic surgical systems with alternative setup conditions while using a graphical user interface that assists the user with instrument connections. For example, by indicating which instrument ports are available and/or unavailable for instrument connections, the systems and methods herein help reduce errors in improper instrument connections and save time by simplifying the procedure of setting up the system. By graphically indicating which ports are available and/or unavailable, the person setting up the machine is more likely to connect an instrument to a correct instrument port. For example, in the event of a combined function system to which an anterior-only cassette is installed for anterior-only procedures, the user making instrument connections is aided by the display indicating which ports are available or unavailable. Systems and methods as disclosed herein provide ease of use, help avoid confusion, and result in a more efficient procedure of setting up the system. The systems and methods disclosed herein thereby save time and cost and help prevent errors.

For these reasons, the graphical user interfaces as described herein improve the functioning of the ophthalmic surgical systems. The graphical user interfaces as described herein solve the technical problem of improper or delayed connections of desired instruments. The graphical user interfaces as described herein make the set up and use of the ophthalmic surgical systems more efficient, reduce errors, and save time and cost.

Persons of ordinary skill in the art will appreciate that the implementations encompassed by the disclosure are not limited to the particular exemplary implementations described above. In that regard, although illustrative implementations have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. An ophthalmic surgical system, the ophthalmic surgical system comprising:
  an ophthalmic surgical console comprising a host computer;
  a display screen; and
  a plurality of instruments configured to be connected to the ophthalmic surgical console;
  wherein the ophthalmic surgical system has a plurality of alternative setup conditions;
  wherein the host computer is configured to detect a setup condition of the ophthalmic surgical system from the plurality of alternative setup conditions of the ophthalmic surgical system based upon at least one of a configuration of the ophthalmic surgical system or a type of fluidics cassette installed on the ophthalmic surgical console;
wherein the configuration is determined based on one or more functional modules coupled with the ophthalmic surgical console;
wherein the alternative setup conditions of the ophthalmic surgical system include:
an anterior-only condition;
a posterior-only condition; and
a combined function condition; and
wherein the host computer is configured to display on the display screen a graphical user interface corresponding to the detected setup condition,
wherein the graphical user interface indicates one or more available instrument ports for a surgical procedure based on the detected setup condition determined from the at least one of the configuration determined based on the one or more functional modules coupled with the surgical console or the type of fluidics cassette installed on the ophthalmic surgical console, the one or more available instrument ports comprising all or some of a plurality of instrument ports on the ophthalmic surgical console.

2. An ophthalmic surgical system as in claim 1, wherein the ophthalmic surgical console is capable of being configured as an anterior-only machine or as a combined function machine, and wherein the alternative setup conditions of the ophthalmic surgical system include the anterior-only condition when the ophthalmic surgical console is configured as the anterior-only machine and the combined function condition when the ophthalmic surgical console is configured as the combined function machine.

3. An ophthalmic surgical system as in claim 1, wherein the ophthalmic surgical system is modular and configured to accommodate different functional modules based on a desired setup condition.

4. An ophthalmic surgical system as in claim 3, wherein the modular ophthalmic surgical system can accommodate the different functional modules to support at least one of the plurality of alternative setup conditions of the ophthalmic surgical console, wherein each of the plurality of alternative setup conditions is suitable to perform a different surgical procedure.

5. An ophthalmic surgical system as in claim 1, wherein the type of fluidics cassette includes two or more of the following: an anterior-only cassette, a posterior-only cassette, and a combined function cassette.

6. An ophthalmic surgical system as in claim 1, wherein the alternative setup conditions of the ophthalmic surgical system include two or more of the following conditions: the anterior-only condition when an anterior-only cassette is installed on the ophthalmic surgical console, the posterior-only condition when a posterior-only cassette is installed on the ophthalmic surgical console, and the combined function condition when a combined function cassette is installed on the ophthalmic surgical console.

7. An ophthalmic surgical system as in claim 1, wherein the host computer is configured to display on the display screen a graphical user interface that graphically indicates one or more incorrect instrument ports for the surgical procedure that are not available for instrument connections in the detected setup condition of the ophthalmic surgical system.

8. An ophthalmic surgical system as in claim 1, wherein the host computer is configured to display on the display screen a graphical user interface that graphically indicates the instrument ports to which instruments are connected.

9. An ophthalmic surgical system as in claim 1, wherein the display screen is part of the ophthalmic surgical console.

10. An ophthalmic surgical system, the ophthalmic surgical system comprising:
an ophthalmic surgical console comprising a host computer, wherein the ophthalmic surgical console is capable of being configured at least as an anterior-only machine or as a combined function machine;
a display screen; and
a plurality of fluidics cassettes that are configured to be installed on the ophthalmic surgical console, wherein the ophthalmic surgical console is configured to have installed on it one fluidics cassette at a time;
wherein the ophthalmic surgical system has a plurality of alternative setup conditions based upon whether the ophthalmic surgical console is configured as the anterior-only machine or as the combined function machine and based upon which cassette of the plurality of fluidics cassettes is installed on the ophthalmic surgical console;
wherein the host computer is configured to detect a setup condition of the ophthalmic surgical system from the plurality of alternative setup conditions of the ophthalmic surgical system based upon at least one of a configuration of the ophthalmic surgical system or a type of fluidics cassette installed on the ophthalmic surgical console;
wherein the configuration is determined based on one or more functional modules coupled with the ophthalmic surgical console;
wherein the alternative setup conditions of the ophthalmic surgical system include:
an anterior-only condition;
a posterior-only condition; and
a combined function condition; and
wherein the host computer is configured to display on the display screen a graphical user interface corresponding to the detected setup condition,
wherein the graphical user interface indicates one or more available instrument ports for a surgical procedure based on the detected setup condition determined from the at least one of the configuration determined based on the one or more functional modules coupled with the surgical console or the type of fluidics cassette installed on the ophthalmic surgical console, the one or more available instrument ports comprising all or some of a plurality of instrument ports on the ophthalmic surgical console.

11. A method of displaying a graphical user interface in an ophthalmic surgical system, the method comprising:
detecting a setup condition of the ophthalmic surgical system from a plurality of alternative setup conditions of the ophthalmic surgical system based upon at least one of a configuration of the ophthalmic surgical system or a type of fluidics cassette installed on an ophthalmic surgical console;
wherein the configuration is determined based on one or more functional modules coupled with the ophthalmic surgical console;
wherein the alternative setup conditions of the ophthalmic surgical system include:
an anterior-only condition;
a posterior-only condition; and
a combined function condition; and displaying on a display screen a graphical user interface corresponding to the detected setup condition, wherein the graphical user interface indicates one or more available instrument ports for a surgical procedure based on the detected setup condition determined from the at least one of the configuration determined based on the one or more functional modules coupled with the surgical console or the type of fluidics cassette installed on the ophthalmic surgical console, the one or more available instrument ports comprising all or some of a plurality of instrument ports on the ophthalmic surgical console.

12. A method of displaying a graphical user interface in an ophthalmic surgical system as in claim 11, wherein the ophthalmic surgical system comprises the ophthalmic surgical console, wherein the ophthalmic surgical console is capable of being configured at least as an anterior-only machine or as a combined function machine, and wherein the alternative setup conditions of the ophthalmic surgical system include the anterior-only condition when the ophthalmic surgical console is configured as the anterior-only machine and the combined function condition when the ophthalmic surgical console is configured as the combined function machine.

13. A method of displaying a graphical user interface in an ophthalmic surgical system as in claim 11, wherein the method further comprises:

prior to the step of detecting the setup condition of the ophthalmic surgical system, installing a fluidics cassette on the ophthalmic surgical console of the ophthalmic surgical system; and wherein the step of detecting the setup condition of the ophthalmic surgical system comprises detecting the setup condition of the ophthalmic surgical system based upon which cassette of a plurality of fluidics cassettes is installed on the ophthalmic surgical console.

14. A method of displaying a graphical user interface in an ophthalmic surgical system as in claim 11, wherein the step of displaying on the display screen the graphical user interface corresponding to the detected setup condition comprises graphically indicating correct instrument ports that are available for instrument connections in the detected setup condition of the ophthalmic surgical system.

15. A method of displaying a graphical user interface in an ophthalmic surgical system as in claim 11, wherein the step of displaying on the display screen the graphical user interface corresponding to the detected setup condition comprises graphically indicating one or more incorrect instrument ports for the surgical procedure that are not available for instrument connections in the detected setup condition of the ophthalmic surgical system.

16. A method of displaying a graphical user interface in an ophthalmic surgical system as in claim 11, wherein the step of displaying on the display screen the graphical user interface corresponding to the detected setup condition comprises graphically indicating instrument ports to which instruments are connected.

\* \* \* \* \*